United States Patent [19]

Lukas et al.

[11] Patent Number: 4,762,715
[45] Date of Patent: Aug. 9, 1988

[54] ANTIHERPETICALLY ACTIVE LIPSTICK AND THE USE THEREOF FOR THE TREATMENT OF DISORDERS OF THE LIPS AND OTHER AREAS OF THE FACE CASUED BY HUMAN HERPES VIRUSES

[75] Inventors: Bohumir Lukas; Franz X. Fischer, both of Basel; Elfy Aeschlimann, Riehen, all of Switzerland

[73] Assignee: Ciba-Geigy Corporation, Ardsley, N.Y.

[21] Appl. No.: 110,648

[22] Filed: Oct. 15, 1987

Related U.S. Application Data

[63] Continuation of Ser. No. 767,939, Aug. 21, 1985, abandoned, which is a continuation of Ser. No. 284,749, Jul. 20, 1981, abandoned.

[30] Foreign Application Priority Data

Jul. 30, 1980 [CH] Switzerland .................. 5810/80
Oct. 2, 1980 [CH] Switzerland .................. 7361/80

[51] Int. Cl.$^4$ ............................................. A61K 33/30
[52] U.S. Cl. ...................................... 424/145; 514/56; 514/934
[58] Field of Search ......................... 514/56; 424/145

[56] References Cited

U.S. PATENT DOCUMENTS 4,226,889 10/1980 Yuhas ................................. 424/145
4,465,666 8/1984 Lukas ................................. 424/145

FOREIGN PATENT DOCUMENTS 0012115 of 1979 European Pat. Off. .

OTHER PUBLICATIONS

The Merck Index, 9th ed., Merck and Co. Inc., Rahway, N.J., 1976, Entry No. 4510.
U.S. Pharmacopeia (1980), p. 1249.
Bohme et al, Deutsches Arzneibuch (1978), p. 639.
Webster's Third New International Dictionary, vol. 1: p. 180 (1965).

Primary Examiner—J. R. Brown
Assistant Examiner—F. T. Moezie
Attorney, Agent, or Firm—Irving M. Fishman

[57] ABSTRACT

The invention relates to an antiherpetic lipstick which is characterized by a content of an antiherpetically active combination of at least one sulphatised polysaccharide or sulphatized polymer, or at least one salt thereof, for example heparin sodium, and a dissociable zinc salt, for example zinc sulphate heptahydrate, in admixture with a polyethylene glycol mixture of which the constituents have a molecular weight of between 300 and 4000. Such lipsticks may contain further additives, especially polyoxyethylene sorbitan fatty acid esters or sorbitan fatty acid esters. The invention relates also to the use of these lipsticks for the treatment of disorders of the lips and of other areas of the face caused by human herpes viruses.

16 Claims, No Drawings

ANTIHERPETICALLY ACTIVE LIPSTICK AND THE USE THEREOF FOR THE TREATMENT OF DISORDERS OF THE LIPS AND OTHER AREAS OF THE FACE CASUED BY HUMAN HERPES VIRUSES

This application is a continuation of application Ser. No. 767,939, filed Aug. 31, 1985, now abandoned, which is a continuation of Ser. No. 284,749, filed July 20, 1981, now abandoned.

The invention relates to a novel antiherpetically active lipstick and the use thereof for the treatment of disorders of the lips and other areas of the face caused by human herpes viruses.

Pharmaceutical preparations for the topical treatment of virus infections, especially infections caused by herpes viruses and more especially by herpesvirus hominis, that contain an antivirally active combination of a sulphatised polysaccharide or a sulphatised polymer, or salts thereof, and zinc ions in the form of dissociable zinc salts, are known from EU-OS Nos. 0 000 133 and 0 012 115. These specifications also describe various forms of topical application that are customary per se, such as tinctures, solutions, creams, ointments and gels.

*Herpes labialis* is a particularly common and aesthetically disturbing herpes disorder. Lipsticks that contain the above combination of active substances could also be considered as suitable forms of topical application for the treatment of *Herpes labialis*, since increasing use is being made of lipsticks also in the field of skin-care cosmetics, that is to say, for the application of skin-care and protective substances. Our own tests have shown, however, that in the known lipstick bases used in beauty and skin-care cosmetics, the above-mentioned combination of active substances does not develop the strong action known, for example, from its use in the form of gels, but has a considerably weaker action because constituents of these bases, for example waxes, higher fatty alcohols and fats per se tend rather to promote infectivity and the formation of vesicles and to delay healing.

Surprisingly, a base has now been found which is suitable in its consistency and other characteristics for the manufacture of lipsticks and in which the effectiveness of the above-mentioned combination of active substances is fully retained. The antiherpetic lipstick according to the invention based on this knowledge is characterised by a content of an antiherpetically active combination of at least one sulphatised polysaccharide or sulphatised polymer, or at least one salt thereof, and a dissociable zinc salt, in admixture with a polyethylene glycol mixture of which the constituents have a molecular weight of between 300 and 4000. The invention relates also to the use of this lipstick for the treatment of disorders of the lips and other areas of the face caused by human herpes viruses.

Like the forms of application described in the patent specifications mentioned above, also in the antiherpetic lipsticks according to the present invention the synergistic action of the two active substance constituents may additionally be increased by adding to the two active substance constituents one or more polyoxyethylene sorbitan fatty acid esters, especially polyoxyethylene sorbitan monostearate, monolaurate and/or monooleate. It is also possible to add other surface-active substances, such as, for example, sorbitan monostearate, monolaurate and/or monooleate.

Sulphatised polysaccharides are understood to mean polysaccharides in which monovalent sulphuric acid radicals $-SO_2-OH$ are bonded to oxygen atoms and/or, if present, as in heparin, nitrogen atoms. Such sulphatised polysaccharides may be of natural origin, such as heparin, chondroitin sulphate (chondroitin sulphuric acid) or carrageenin, or may be prepared by sulphatisation of natural or partially degraded polysaccharides, such as sulphatised amylopectins, sulphatised dextrans, sulphatised polyglucoses or sulphatised polypentoses, preferably in the form of suitable, pharameutically acceptable salts such as, for example, potassium, and especially, sodium salts. As such salts there may be mentioned the sodium salt of heparin, this being the customary commercial form of the latter, also the potassium, lithium, ammonium and magnesium salt of heparin, and the sodium salts of sulphatised dextrans. Sulphatised polymers are sulphatisation products of polymers containing hydroxy groups, such as, for example, sulphatised polyvinyl alcohols (polyvinyl sulphates) of different average molecular size which, in their turn, are preferably used in the form of pharmaceutically acceptable salts, such as the sodium or potassium salts.

As dissociable zinc salts there may be used, for example, zinc sulphate and hydrates thereof, especially the heptahydrate, $ZnSO_4.7H_2O$, or a different dissociable zinc salt, such as, for example, zinc chloride, zinc acetate or zinc citrate, or the zinc salt of an acid or of another substance that is of acidic character and has its own biological, for example antibacterial or antiphlogistic, properties, such as, for example, zinc sudoxicam (zinc salt of 4-hydroxy-2-methyl-N-(2-thiazolyl)-1,2-benzothiazin-3-carboxamide-1,1-dioxide).

Preferred lipstic bases may be obtained by combining a liquid polyethylene glycol (PEG) having a low molecular weight with solid PEG having a higher molecular weight. As PEG having a low molecular weight there come into consideration especially those having an average molecular weight of between 300 and 400, and as PEG having a higher molecular weight those having an average molecular weight of between 1000 and 4000 are preferred. Mixtures of PEG 400 and PEG 1000 with a small addition of PEG 4000 are especially suitable. Depending on the types of PEG used, the proportions of liquid PEG to solid PEG lie preferably between 15+85 and 30+70 parts. Using these PEG mixtures lipsticks are obtained that have a stable shape and in use ensure an appropriate amount is rubbed onto the lips or areas of the face to be treated.

The lipstick according to the invention may also contain small quantities of polyethylene glycols having a molecular weight of more than 4000, glycerine and customary additives, such as colouring agents, aromatic substances, perfumes and light-protective agents. It is also possible to add substances that promote tissue regeneration (for example allantoin). It is not necessary to add preservatives as the lipstick according to the invention has self-preserving properties.

The present invention relates especially to lipsticks that contain sulphatised polysaccharides, or sulphatised polymers, or salts thereof, such as heparin sodium, and zinc ions in the form of dissociable zinc salts in a ratio of 1 mg : 0.18 to 4.5 gm, and optionally polyoxyethylene sorbitan monostearate, monolaurate and/or monooleate, or sorbitan monostearate, monolaurate and/or monooleate. In the case of heparin sodium the above quantities relate to heparin sodium having 160 USP units/mg; in the case of a different type of heparin sodium the same USP unit quantities are to be used. The above quantity range of zinc ions corresponds, for example, in the case of zinc sulphate heptahydrate, $ZnSO_4.7H_2O$, in the form of a dissociable zinc salt, to a quantity range of from 0.8 to 20 mg. Such lipsticks contain, for example, per g, from 0.2 to 10 mg, especially from 1 to 5 mg of a sulphatised polysaccharide or sulphatised polymer, or of a salt thereof, for example from 32 to 1600 USP units, especially from 80 to 800 USP units, of heparin sodium, and from 0.18 to 18 mg of zinc ions, corresponding to, for example, approximately 0.8 to 80 mg of $ZnSO_4.7H_2O$, and optionally, in addition, a total of from 0.2 to 50 mg of polyoxyethylene sorbitan monostearate, monolaurate and/or monooleate, or of sorbitan monostearate, monolaurate and/or monooleate. Especially preferred is a content, per g or ml, of from 160 to 480 USP units of heparin sodium, from 0.45 to 4.5 mg of zinc ions in the form of dissociable zinc salts and optionally, in addition, a total of from 1.0 to 20 mg of polyoxyethylene sorbitan monostearate, monolaurate and/or monooleate, or of sorbitan monostearate, monolaurate and/or monooleate.

Instead of heparin or salts thereof it is also possible to use a quantity, having the same antiherpetic action, of a different sulphatised polysaccharine or of a sulphatised polymer or of one of the salts thereof.

For the treatment of herpes of the lips and other areas of the face, the lipstick according to the invention is applied to the affected lips as early as possible several times daily until the symptoms disappear or until the affected areas are completely healed.

The following Examples describe the preparation of a lipstick; they are not in any way to restrict the scope of the invention, however.

EXAMPLE 1

10 kg of lipstick composition are prepared by melting together 7.73 kg of polyethylene glycol 1000 and 190 g of polyethylene glycol 4000 with 1.4 kg of polyethylene glycol 400, 160 g of polyoxyethylene sorbitan monostearate (TWEEN 60) and 40 g of polyoxyethylene sorbitan monooleate (TWEEN 80). 80 g of very finely ground heparin sodium (having a biological activity of 160 USP units/mg) are then mixed with 400 g of very finely ground zinc sulphate heptahydrate ($ZnSO_4.7H_2O$). This powder mixture is then dispersed in the base melt by stirring vigorously. Casting in lipstick moulds is effected at a temperature just above the setting point.

TWEEN 60 and TWEEN 80 are protected brand names of ICI of America Inc., Stamford, Connecticut (USA).

EXAMPLE 2

Lipsticks are prepared analogously to Example 1 but using the following amounts of active substances and adjuncts:

6.76 kg of polyethylene glycol 3000, 2.90 kg of polyethylene glycol 300, 80 g of polyoxyethylene sorbitan monostearate (TWEEN 60), 20 g of polyoxyethylene sorbitan monooleate (TWEEN 80), 40 g of very finely ground heparin sodium and 200 g of very finely ground zinc sulphate heptahydrate.

EXAMPLE 3

Lipsticks are prepared analogously to Example 1 but using the following amounts of active substances and adjuncts:

6.60 kg of polyethylene glycol 3000, 2.91 kg of polyethylene glycol 300, 200 g of glycerine 98%, 40 g of polyoxyethylene sorbitan monostearate (TWEEN 60), 10 g of polyoxyethylene sorbitan monooleate (TWEEN 80), 40 g of very finely ground heparin sodium and 200 g of very finely ground zinc sulphate heptahydrate.

EXAMPLE 4

Lipsticks are prepared analogously to Example 1 but using the following amounts of active substances and adjuncts:

6.88 kg of polyethylene glycol 3000, 2.95 kg of polyethylene glycol 400, 40 g of polyoxyethylene sorbitan monostearate (TWEEN 60), 10 g of polyoxyethylene sorbitan monooleate (TWEEN 80), 20 g of very finely ground heparin sodium and 100 g of very finely ground zinc sulphate heptahydrate.

EXAMPLE 5

Lipsticks are prepared analogously to Example 1 but using the following amounts of active substances and adjuncts:

7.553 kg of polyethylene glycol 1000, 246 g of polyethylene glycol 4000, 1.946 kg of polyethylene glycol 400, 60 g of polyoxyethylene sorbitan monostearate (TWEEN 60), 15 g of polyoxyethylene sorbitan monooleate (TWEEN 80), 30 g of very finely ground heparin sodium and 150 g of very finely ground zinc sulphate heptahydrate.

EXAMPLE 6

Lipsticks are prepared analogously to Example 1 but using the following amounts of active substances and adjuncts:

7.600 kg of polyethylene glycol 1000, 248 g of polyethylene glycol 4000, 1.957 kg of polyethylene glycol 400, 60 g of polyoxyethylene sorbitan monostearate (TWEEN 60), 15 g of polyoxyethylene sorbitan monooleate (TWEEN 80), 30 g of very finely ground heparin sodium and 90 g of very finely ground zinc sulphate heptahydrate.

EXAMPLE 7

Lipsticks are prepared analogously to Example 1 but using the following amounts of active substances and adjuncts:

7.80 kg of polyethylene glycol 1000, 200 g of polyethylene glycol 4000, 1.520 kg of polyethylene glycol 400, 200 g of glycerine 98%, 80 g of polyoxyethylene sorbitan monostearate (TWEEN 60), 20 g of polyoxyethylene sorbitan monooleate (TWEEN 80), 30 g of very finely ground heparin sodium and 150 g of very finely ground zinc sulphate heptahydrate.

EXAMPLE 8

Lipsticks are prepared analogously to Example 7 but using sorbitan monostearate (SPAN 60) instead of polyoxyethylene sorbitan monostearate, and sorbitan monooleate (SPAN 80) instead of polyoxyethylene sorbitan monooleate.

We claim:
1. An antiherpetic lipstick consisting of
(A) a lipstick base consisting of a mixture in a weight ratio of from 15:85 to 30:70 of a liquid polyethylene glycol of an average molecular weight of 300–400 and of a solid polyethylene glycol of an average molecular weight of 1000–4000; and

(B) an antiherpetically effective amount of the active component consisting of a mixture, in weight ratio, of from 1:0.18 to 1:4.5 of heparin or a pharmaceutically acceptable salt thereof in a quantity equivalent to 32 to 1600 USP units of heparin sodium for 1 g of the lipstick, and of zinc ions provided in the form of a dissociable zinc salt; and, (C) a member, in an amount of zero mg or in an amount of 0.2-50 mg per 1 g of the lipstick, which member is selected from a group consisting of polyoxyethylene sorbitan monostearate, polyoxyethylene sorbitan monolaurate, polyoxyethylene sorbitan monooleate, sorbitan monostearate, sorbitan monolaurate and sorbitan monooleate 2. An antiherpetic lipstick according to claim 1 wherein the sulphatised polysaccharid is heparin sodium of 160 USP units/mg.

3. An antiherpetic lipstick according to claim 1 wherein the zinc ions are in the form of zinc sulphate heptahydrate.

4. An antiherpetic lipstick according to claim 1 wherein the antiherpetically effective amount of the active component B comprises, per 1 g of the lipstick, from 0.2 to 10 mg of the sulphatised polysaccharid, and from 0.18 to 18 mg of zinc ions.

5. An antiherpetic lipstick according to claim 1 wherein the antiherpetically effective amount of the active component B comprises, per 1 g of the lipstick, from 1 to 5 mg of the sulphatised polysaccharid, and from 0.18 to 18 mg of zinc ions.

6. An antiherpetic lipstick according to claim 5 which contains said component C in a total amount of 0.2-50 mg per 1 g of the lipstick.

7. An antiherpetic lipstick according to claim 1 wherein the antiherpetically effective amount of the active component B is per 1 g of the lipstick, from 32 to 1600 USP units of heparin sodium and 0.18 to 18 mg of zinc ions.

8. An antiherpetic lipstick according to claim 7 wherein the zinc ions are in the form of zinc sulphate heptahydrate.

9. An antiherpetic lipstick according to claim 1 wherein the antiherpetically effective amount of the active component B is per 1 g of the lipstick, from 80 to 800 USP units of heparin sodium and 0.18 to 18 mg of zinc ions.

10. An antiherpetic lipstick according to claim 9 wherein the zinc ions are in the form of zinc sulphate heptahydrate.

11. An antiherpetic lipstick according to claim 9 which contains said component C in a total amount of 0.2-50 mg per 1 g of the lipstick.

12. An antiherpetic lipstick according to claim 1 wherein the antiherpetically effective amount of the active component B is per 1 g of the lipstick, from 160 to 480 USP units of heparin sodium and 0.45 to 4.5 mg of zinc ions.

13. An antiherpetic lipstick according to claim 12 wherein the zinc ions are in the form of zinc sulphate heptahydrate.

14. An antiherpetic lipstick according to claim 12 which contains said component C in a total amount of 1.0-20 mg per 1 g of the lipstick.

15. An antiherpetic lipstick according to claim 1 wherein said liquid polyethylene glycol is polyethylene glycol 400; and said solid polyethylene glycol is a mixture consisting of a major portion of polyethylene glycol 1000 and a minor portion of polyethylene glycol 4000.

16. A method of treatment of disorders of the lips and other areas of the face caused by human herpes viruses which comprises applying to said areas an antiherpetically effective amount of the lipstick defined in claim 1.

* * * * *